United States Patent
Tanaka et al.

(10) Patent No.: US 10,219,679 B2
(45) Date of Patent: Mar. 5, 2019

(54) ENDOSCOPE

(71) Applicant: FUJIFILM Corporation, Tokyo (JP)

(72) Inventors: Toshizumi Tanaka, Kanagawa (JP);
Tomohiro Ohki, Kanagawa (JP);
Teruyuki Emura, Kanagawa (JP);
Sunao Hachisuka, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/073,659

(22) Filed: Mar. 18, 2016

(65) Prior Publication Data
US 2016/0270630 A1    Sep. 22, 2016

(30) Foreign Application Priority Data
Mar. 20, 2015 (JP) .................................. 2015-058346

(51) Int. Cl.
*A61B 1/00* (2006.01)

(52) U.S. Cl.
CPC ...... *A61B 1/00098* (2013.01); *A61B 1/00137* (2013.01)

(58) Field of Classification Search
CPC .................. A61B 1/00098; A61B 1/00101
USPC .................. 600/106, 107, 127, 133
See application file for complete search history.

(56) References Cited

U.S. PATENT DOCUMENTS

| | | | | | |
|---|---|---|---|---|---|
| 5,562,600 | A | * | 10/1996 | Matsuno | A61B 1/018 600/107 |
| 5,573,494 | A | * | 11/1996 | Yabe | A61B 1/00091 600/104 |
| 6,004,264 | A | * | 12/1999 | Sano | A61B 1/00126 600/131 |
| 2001/0044570 | A1 | * | 11/2001 | Ouchi | A61B 1/00098 600/107 |

(Continued)

FOREIGN PATENT DOCUMENTS

| | | |
|---|---|---|
| JP | H0664609 | 9/1994 |
| JP | H114804 | 1/1999 |

(Continued)

OTHER PUBLICATIONS

"Office Action of Japan Counterpart Application," dated Nov. 24, 2017, with English translation thereof, p. 1-p. 6.

(Continued)

*Primary Examiner* — Alexandra L Newton
*Assistant Examiner* — Rynae Boler
(74) *Attorney, Agent, or Firm* — JCIPRNET

(57) ABSTRACT

An endoscope which can reduce time and labor for cleaning processing is provided. The endoscope includes: a distal end portion body which is provided on the distal end side of an insertion portion; a rotating shaft which is rotatably supported in the distal end portion body; an elevator which is coupled with one end of the rotating shaft; an elevator erecting lever which is coupled with the other end of the rotating shaft; an operating wire which rotates the rotating (Continued)

shaft through the elevator erecting lever by operation of an operating member and raises the elevator; a partition wall which includes a holding hole to support the rotating shaft; and a seal member which is disposed between the holding hole and the rotating shaft, at least part of the seal member being exposed to a surface side facing the elevator of the partition wall.

10 Claims, 11 Drawing Sheets

(56) References Cited

U.S. PATENT DOCUMENTS

2004/0082836 A1   4/2004   Hino

FOREIGN PATENT DOCUMENTS

| JP | 2004-141315 | 5/2004 |
| JP | 2010-201020 | 9/2010 |
| JP | 2014-046167 | 3/2014 |
| JP | 2014132923 | 7/2014 |

OTHER PUBLICATIONS

"Notice of allowance of Japan Counterpart Application," dated Jun. 27, 2018, with English translation thereof, p. 1-p. 6.
"Office Action of China Counterpart Application," dated Oct. 23, 2018, with English translation thereof, p. 1-p. 15.

* cited by examiner

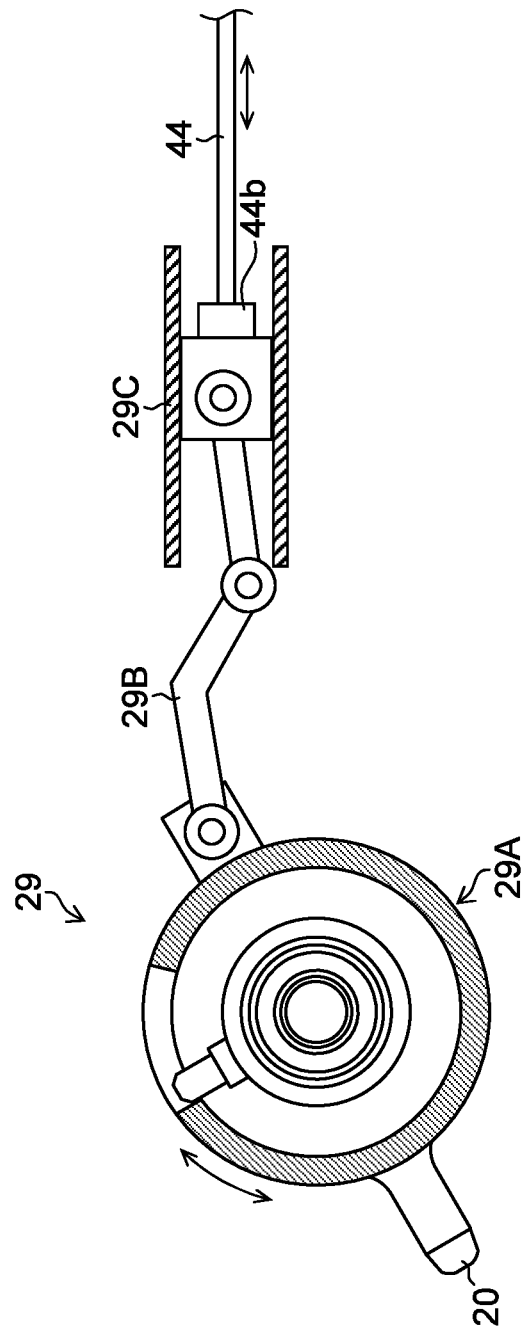

ENDOSCOPE

CROSS-REFERENCE TO RELATED APPLICATIONS

The present application claims priority under 35 U.S.C. § 119 to Japanese Patent Application No. 2015-058346, filed on Mar. 20, 2015. Each of the above application(s) is hereby expressly incorporated by reference, in their entirety, into the present application.

BACKGROUND OF THE INVENTION

Field of the Invention

The present invention relates to an endoscope including an elevator that controls the derivation direction of a treatment tool, in a distal end portion of an insertion portion.

Description of the Related Art

In an endoscope, various treatment tools are inserted in a treatment tool entry port provided in an operation portion, are led out from a treatment tool exit port opened in a distal end portion and are used for treatment. For example, various treatment tools are used such as a guide wire or a contrast tube in a duodenoscope, and a puncture needle in an ultrasonic endoscope, and, additionally, a forceps and a snare in a direct-view endoscope or a side-view endoscope. In such treatment tools, it is necessary to change the derivation direction in a distal end portion to treat a desired position in a subject, and, therefore, a treatment tool elevating mechanism (forceps elevator, hereinafter referred to as "elevator") is provided in the distal end portion.

As such a treatment tool elevating mechanism, there is known a mechanism in which an operating wire is attached to an elevator and extended to the proximal end side of an endoscope, and the elevator is rotated around a rotating shaft by performing push-pull operation on the operating wire with an operating lever provided in an operation portion so as to change the position of the elevator between a erecting position and a reclining position. Moreover, there is known a so-called lever-type mechanism in which an elevator erecting lever which is housed with an elevator across a partition wall is coupled to the elevator with a rotating shaft, an operating wire is attached to the elevator erecting lever, and the elevator is rotated around the rotating shaft by pushing and pulling the operating wire with an operating lever included in an operation portion so as to change the position of the elevator between a erecting position and a reclining position (see Japanese Patent Application Laid-Open No. 2014-046167, Japanese Patent Application Laid-Open No. 2010-201020, and Japanese Patent Application Laid-Open No. 2004-141315).

SUMMARY OF THE INVENTION

By the way, in an endoscope, it is necessary to perform cleaning processing using a cleaning solution or an antiseptic solution every time it is used for various inspections or treatments. At this time, since a body of the distal end portion (distal end portion body) including a treatment tool elevating mechanism is miniaturized and its shape is complicated, the improvement of cleaning performance and the easiness of cleaning work, which are associated with the flow of the cleaning solution or the antiseptic solution, the insertion performance of a cleaning brush and the draining performance and so on, are requested. In particular, there is a problem that, when performing cleaning processing of a fitting portion between a holding hole exposed into an elevator housing chamber and a rotating shaft, it takes time and labor for the cleaning processing because the gap of the fitting portion is small.

The present invention has been made considering such circumstances, and it is an object to provide an endoscope which can reduce the time and labor taken for the cleaning processing.

An endoscope to achieve the object of the present invention includes: an insertion portion which includes a distal end and a proximal end; an operation portion which is provided on a proximal end side of the insertion portion and includes an operating member; a distal end portion body which is provided on a distal end side of the insertion portion; a rotating shaft which is rotatably supported in the distal end portion body; an elevator which is coupled with one end of the rotating shaft; an elevator erecting lever which is coupled with the other end of the rotating shaft; an operating wire which includes a proximal-end-side coupling portion coupled with the operating member and a distal-end-side coupling portion coupled with the elevator erecting lever, the operation wire configured to rotate the rotating shaft through the elevator erecting lever by operation of the operating member to erect the elevator; a partition wall which includes a holding hole configured to support the rotating shaft, is a part of the distal end portion body and is provided between the elevator and the elevator erecting lever; and a seal member which is disposed between the holding hole and the rotating shaft, at least part of the seal member being exposed to a surface side facing the elevator of the partition wall.

According to the above endoscope, a liquid is prevented from entering between the inner wall surface of the holding hole and the outer wall surface of the rotating shaft by the seal member, a part of which is exposed to the surface side facing the elevator of the partition wall, and cleaning processing of a fitting portion between the holding hole and the rotating shaft becomes easy.

In an endoscope according to another aspect of the present invention, the partition wall includes a first engagement portion formed in an inner wall surface of the holding hole; and the seal member includes a second engagement portion configured to engage with the first engagement portion. By the first engagement portion and the second engagement portion, it is possible to restrict the position of the seal member in the axis direction of the rotating shaft such that the part of the seal member is exposed to the surface side facing the elevator of the partition wall.

In an endoscope according to another aspect of the present invention, the rotating shaft includes a first engagement portion formed in an outer wall surface facing an inner wall surface of the holding hole; the seal member includes a second engagement portion configured to engage with the first engagement portion; and the partition wall includes a rotating shaft position restricting portion configured to restrict a position of the rotating shaft in an axis direction with respect to the holding hole. It is possible to restrict the position of the seal member in the axis direction of the rotating shaft such that the part of the seal member is exposed to the surface side facing the elevator of the partition wall.

In an endoscope according to another aspect of the present invention, the first engagement portion includes a seal member position restricting portion configured to restrict a position of the seal member in an axis direction of the rotating shaft. A state in which a part of the seal member is exposed to the surface side facing the elevator of the partition wall is maintained.

In an endoscope according to another aspect of the present invention, the seal member position restricting portion includes a restriction surface which is provided in a position opposed to a surface of the seal member facing the elevator, and the restriction surface restricts the position of the seal member in the axis direction of the rotating shaft. A state in which the part of the seal member is exposed to the surface side facing the elevator of the partition wall is maintained.

In an endoscope according to another aspect of the present invention, the seal member includes a first thick portion and a second thick portion which is disposed on a side of the elevator with respect to the first thickness portion (a second thick portion which is disposed at a position nearer to the elevator than the first thickness portion); and the second thick portion is configured so that a thickness of the second thick portion in a direction perpendicular to an axis direction of the rotating shaft is thicker than the first thickness portion.

An endoscope of the present invention can reduce time and labor taken for cleaning processing.

BRIEF DESCRIPTION OF THE DRAWINGS

FIG. 5 is a schematic diagram illustrating one example of an elevator operation mechanism in an operation portion;

DETAILED DESCRIPTION OF THE PREFERRED EMBODIMENTS

Figure 1:
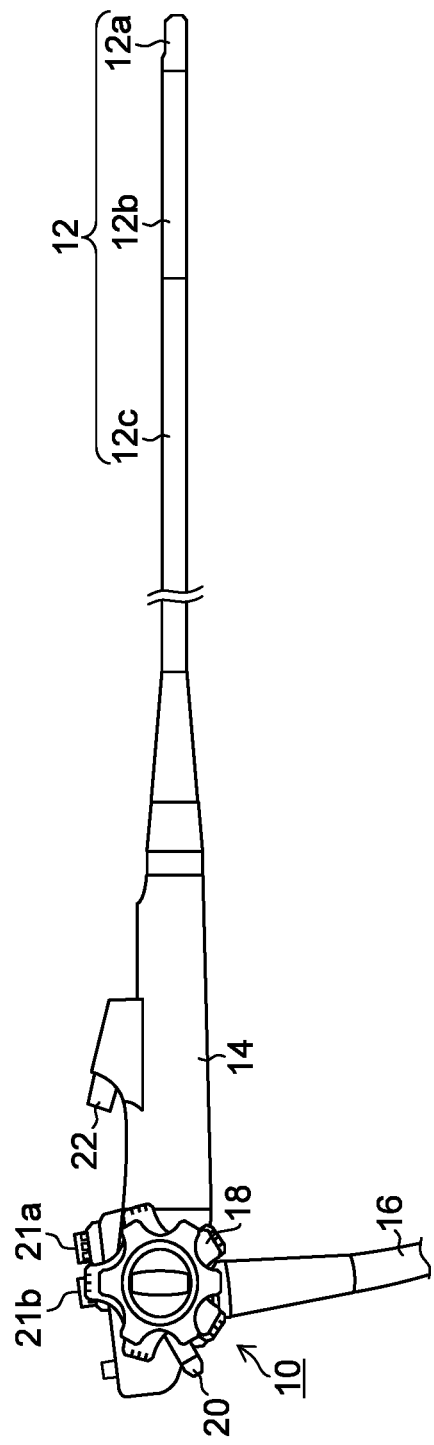
FIG. 1 is a side view illustrating the overall configuration of an endoscope.

An endoscope according to the present invention is described with reference to the accompanying drawings below. FIG. 1 is a side view illustrating an overall configuration of an endoscope 10.

<Overall Configuration of Endoscope>

As illustrated in FIG. 1, the endoscope 10 includes an insertion portion 12 to be inserted in the body of a subject, and an operation portion 14 is coupled with the proximal end side of the insertion portion 12. A universal cord 16 is connected with the operation portion 14, and the endoscope 10 is connected with a light source device, an image processing device (which is also called a processor device) and an air-supply and water-supply device, which are not illustrated in the figure, via the universal cord 16.

<Overall Configuration of Insertion Portion>

The insertion portion 12 is configured by coupling a distal end portion 12a, a bending portion 12b and a flexible portion 12c in this order from the distal end side to the proximal end side (on the side of the operation portion 14). In the insertion portion 12, a treatment tool insertion channel 19 (see FIG. 2) that guides a treatment tool to the distal end portion 12a, an operating wire 44 (see FIG. 2) used to control the derivation direction of the treatment tool led out from the distal end portion 12a, a light guide (not illustrated) that guides illumination light supplied from the light source device to the distal end portion 12a, and an air-supply and water-supply tube (not illustrated) that guides air and water supplied from the air-supply and water-supply device to the distal end portion 12a are inserted.

<Configuration of Operation Portion>

In the operation portion 14, an angle knob 18 to perform bending operation of the bending portion 12b, an elevator operation mechanism 29 (see FIG. 5) including an operating lever 20 described later used for change operation of the derivation direction of a treatment tool led out from the distal end portion 12a, an air-supply and water-supply button 21a to jet air and water, and so on, from an air-supply and water-supply nozzle (not illustrated) provided in the distal end portion 12a, and a suction button 21b to suck a body fluid such as blood from a suction port (not illustrated) provided in the distal end portion 12a, and so on, are provided.

Moreover, a treatment tool entry port 22 to introduce various treatment tools is provided on the side of the insertion portion 12 of the operation portion 14. The distal end of a treatment tool inserted in the treatment tool entry port 22 is led out from a treatment tool exit port 38a (see FIG. 2) provided in the side surface of the distal end portion 12a through the treatment tool insertion channel 19 (see FIG. 2) provided in the insertion portion 12.

<Configuration of Bending Portion>

The bending portion 12b has a configuration in which: a structure is formed by coupling unillustrated angle rings in a mutually rotatable manner; and the outer periphery of this structure is covered with a net-like body woven from metal wire and is further covered with an outer skin made of rubber. A plurality of unillustrated wires extend from the angle knob 18 of the operation portion 14 to the bending portion 12b, and the distal end portions of these wires are fixed to the distal end portions of the angle rings forming the bending portion 12b. By this means, the bending portion 12b is bent in the upper, lower, right or left direction according to the operation of the angle knob 18.

<Configuration of Flexible Portion>

The flexible portion 12c has a configuration in which: the innermost side is a spiral tube is formed by winding an elastic thin belt-shaped plate in a spiral manner, the spiral tube is then covered with a net-like body that is woven from metal wire and fitted with a metal cap at both ends thereof to form a tubular body; the outer peripheral surface of the tubular body is laminated with an outer skin formed of resin.

<Configuration of Distal End Portion>

Figure 2:
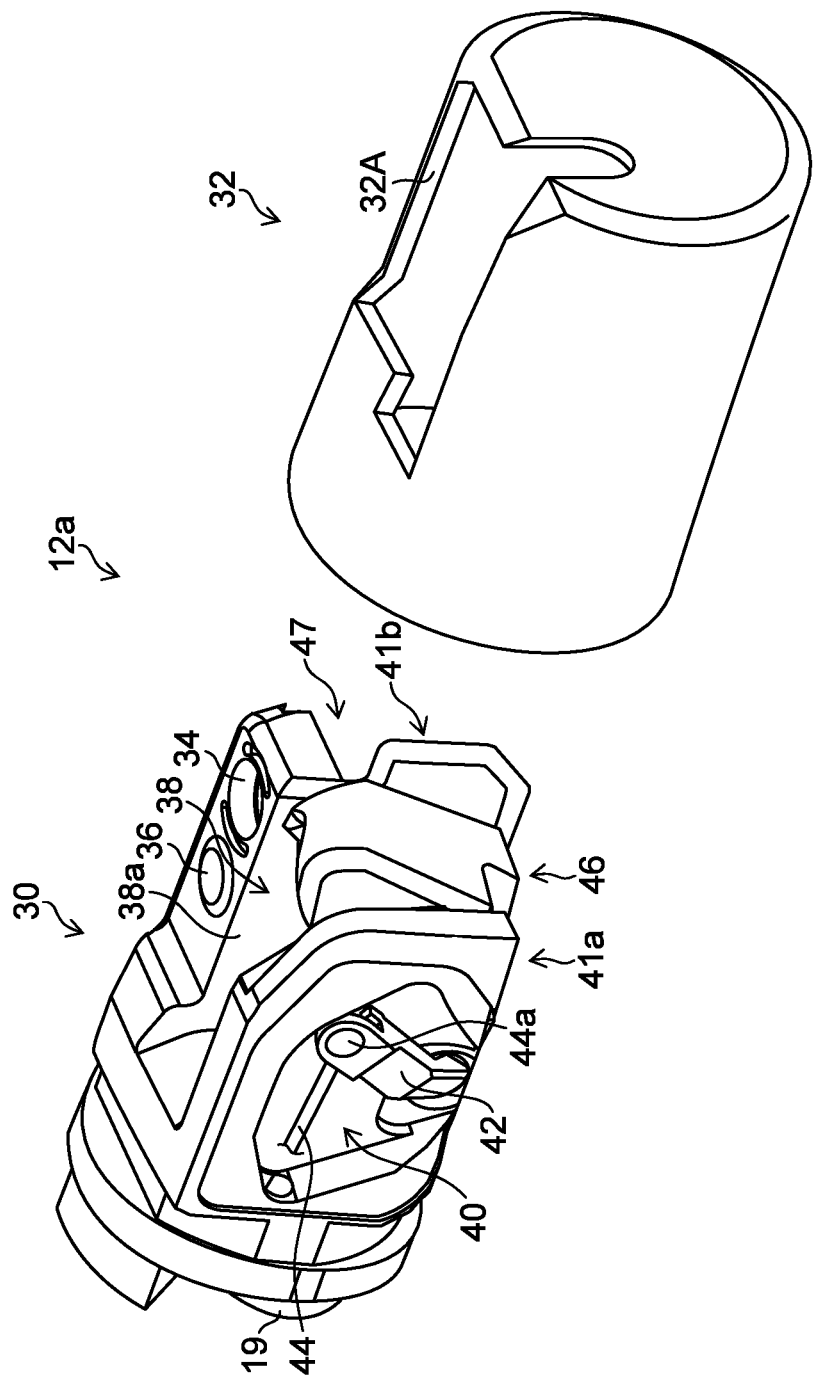
FIG. 2 is an external perspective view illustrating the structure of a distal end portion of an insertion portion.

FIG. 2 is an external perspective view illustrating the structure of the distal end portion 12a. As illustrated in FIG. 2, the distal end portion 12a has a distal end portion body 30 (body 30 of the distal end portion 12a) and a cap 32 which covers the distal end portion body 30. In the cap 32, an opening window 32A which opens the treatment tool exit port 38a that is an opening on the upper surface side of an elevator housing chamber 38 described later is formed in a state where it is attached to the distal end portion body 30. The cap 32 is made of an elastic material, for example, silicone rubber. The cap 32 includes an engagement portion which is engaged with a groove formed in the distal end portion body 30 on the proximal end side thereof and is detachably attached to the distal end portion body 30.

Figure 3:
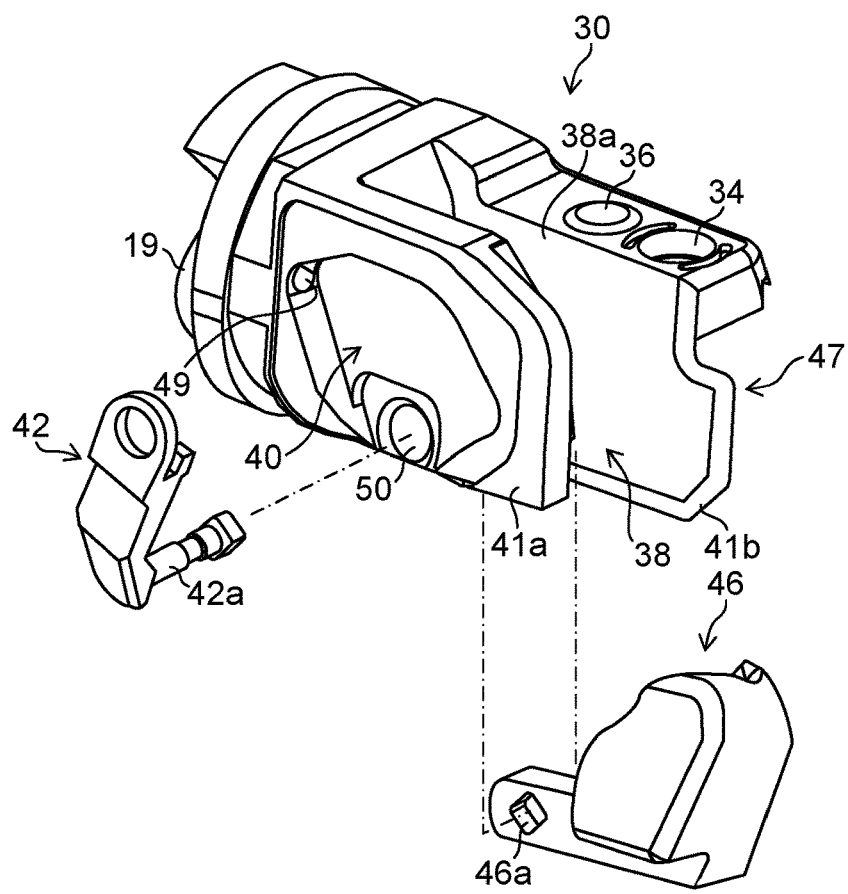
FIG. 3 is an exploded perspective view of the distal end portion.
Figure 4:
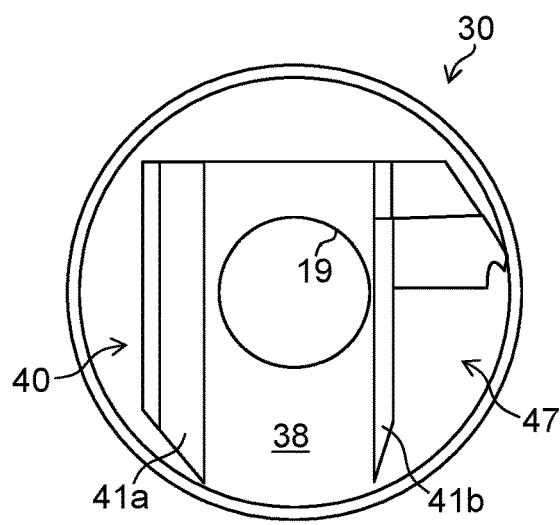
FIG. 4 is a front view of a distal end portion body included in the distal end portion.

FIG. 3 is an exploded perspective view of the distal end portion 12a. FIG. 4 is a front view of the distal end portion body 30. As illustrated in FIGS. 2 to 4, the distal end portion body 30 is formed of a metallic material having corrosion resistance, and includes a pair of a first partition wall 41a and a second partition wall 41b which are parts of the distal end portion body 30 and face each other. The elevator housing chamber 38 that is a slit-like space which houses an elevator 46 is formed between the first partition wall 41a and second partition wall 41b. An opening on the upper surface side of this elevator housing chamber 38 in FIG. 3 is the treatment tool exit port 38a from which the treatment tool is led out.

Moreover, the treatment tool insertion channel 19 communicates with the elevator housing chamber 38 of the distal end portion body 30. This treatment tool insertion channel 19 is connected with the treatment tool entry port 22 of the operation portion 14 through the inside of the insertion portion 12. By this means, when a treatment tool is inserted from the treatment tool entry port 22 to the treatment tool insertion channel 19, the treatment tool is guided into the elevator housing chamber 38 through the treatment tool insertion channel 19.

The elevator 46 changes the direction of the treatment tool guided from the treatment tool insertion channel 19 into the elevator housing chamber 38 and allows the treatment tool to be led out from the treatment tool exit port 38a on the side of the distal end portion body 30. This elevator 46 is swingably attached to the first partition wall 41a through a rotating shaft 42a described later, and, when the treatment tool is led out from the treatment tool exit port 38a, the elevator 46 can control the direction thereof.

The first partition wall 41a corresponds to a partition wall of the present invention. On a side of an opposite surface (opposite surface side) that is a side opposite to a side of a facing surface (facing surface side) facing the elevator housing chamber 38 of the first partition wall 41a, a concave erecting lever housing chamber 40 which houses an elevator erecting lever 42 is formed by notching a part of the opposite surface. In other words, the first partition wall 41a is provided between the elevator 46 (elevator housing chamber 38) and the elevator erecting lever 42 (erecting lever housing chamber 40).

An optical system housing chamber 47 is provided on a side of an opposite surface (opposite surface side) that is a side opposite to a side of a facing surface (facing surface side) facing the elevator housing chamber 38 of the second partition wall 41b. In other words, the second partition wall 41b is provided between the elevator 46 (elevator housing chamber 38) and the optical system housing chamber 47.

Moreover, by covering the distal end portion body 30 with an unillustrated protective plate, the airtightness of each of the erecting lever housing chamber 40 and the optical system housing chamber 47 is maintained.

An illumination window 34 and an observation window 36 are arranged in the upper part of the optical system housing chamber 47, and the air-supply and water-supply nozzle (not illustrated) is provided toward the observation window 36. The air-supply and water-supply nozzle is connected with the above-mentioned air-supply and water-supply device through the air-supply and water-supply tube (not illustrated) inserted in the insertion portion 12. Compressed air or water is jetted from the air-supply and water-supply nozzle toward the observation window 36 by operating the air-supply and water-supply button 21a of the operation portion 14, and the observation window 36 is cleaned.

An illuminating portion and an imaging portion are housed inside the optical system housing chamber 47 though their illustration is omitted. The illuminating portion includes an illumination lens installed on an inner side of the illumination window 34 and a light guide disposed such that the distal end thereof faces this illumination lens. The light guide is inserted in the insertion portion 12 of the endoscope 10, and the proximal end portion thereof is connected with the above-mentioned light source device. By this means, an illumination light from the light source device is transmitted through the light guide and emitted from the illumination window 34.

The imaging portion includes an imaging optical system arranged on an inner side of the observation window 36, and an imaging element of the CMOS (complementary metal oxide semiconductor) type or the CCD (charge coupled device) type. The imaging element is connected with the above-mentioned image processing device through a signal cable inserted in the insertion portion 12. An imaging signal of an object image, which is obtained by imaging by the imaging portion, is input in the above-mentioned image processing device through the signal cable, and the object image is displayed on a monitor of the image processing device.

A holding hole 50 that penetrates through the first partition wall 41a and communicates with the elevator housing chamber 38 is formed in the bottom surface of the concave erecting lever housing chamber 40 which houses the elevator erecting lever 42. The holding hole 50 rotatably supports the rotating shaft 42a described later which couples the elevator 46 and the elevator erecting lever 42. Here, since the elevator erecting lever 42 in the erecting lever housing chamber 40 swings around the rotating shaft 42a, the elevator housing chamber 38 is formed to have a fan-shape having the rotating shaft 42a as a center.

One end side of the elevator erecting lever 42 is coupled with the elevator 46 through the rotating shaft 42a, the other end side of the elevator erecting lever 42 is coupled with the operating wire 44. The elevator erecting lever 42 swings integrally with the elevator 46 around the rotating shaft 42a.

The operating wire 44 includes a distal-end-side coupling portion 44a (see FIGS. 6A and 6B) coupled with the elevator erecting lever 42 in the erecting lever housing chamber 40, on the distal end side thereof. Moreover, the proximal end side of the operating wire 44 is coupled with the elevator operation mechanism 29 (see FIG. 5) in the operation portion 14 through the inside of the insertion portion 12 from a wire insertion hole 49 opened to a wall surface of the erecting lever housing chamber 40.

FIG. 5 is a schematic diagram illustrating one example of the elevator operation mechanism 29 in the operation portion 14. As illustrated in FIG. 5, the operating wire 44 includes a proximal-end-side coupling portion 44b coupled with the elevator operation mechanism 29, on the proximal end side thereof. The elevator operation mechanism 29 corresponds to an operating member of the present invention and includes the operating lever 20, a rotating drum 29A with which the operating lever 20 is coupled and which is rotatable within a certain angle range, a crank member 29B coupled with the rotating drum 29A, and a slider 29C coupled with the crank member 29B. The proximal-end-side coupling portion 44b is coupled with the slider 29C.

When the operating lever 20 is operated to rotate the rotating drum 29A, the elevator erecting lever 42 swings by push-pull operation of the operating wire 44 through the crank member 29B and the slider 29C, and the elevator 46 is displaced between the reclining position and the erecting position according to the swing of the elevator erecting lever 42.

Figure 6A:
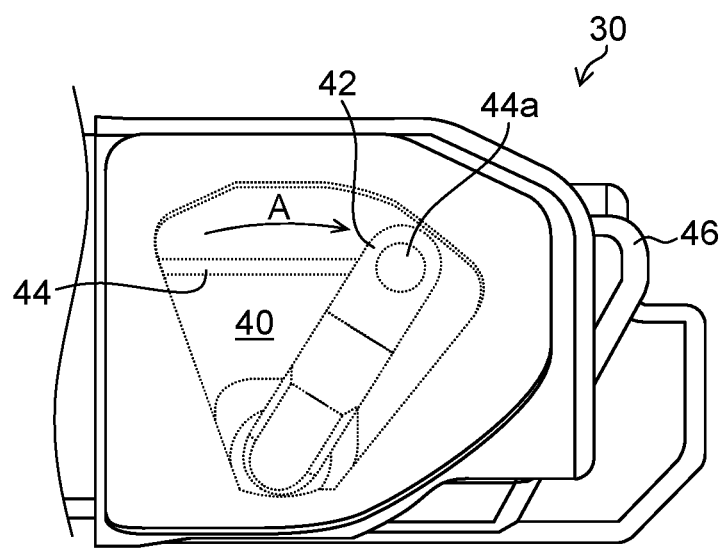
FIGS. 6A and 6B are explanatory diagrams to describe displacement between a reclining position and erecting position of an elevator.
Figure 6B:
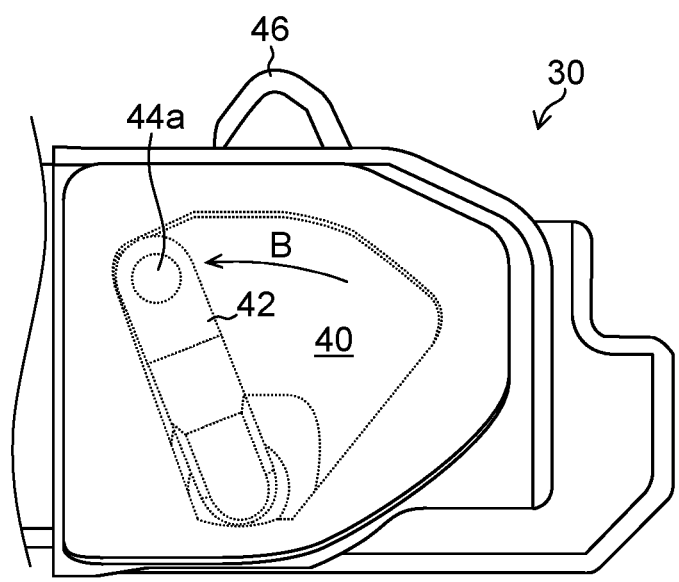

FIGS. 6A and 6B are explanatory diagrams illustrating the displacement between the reclining position and erecting position of the elevator 46. As illustrated in FIG. 6A, by push operation of the operating wire 44 when the operating lever 20 is operated to rotate the rotating drum 29A in one direction, the elevator erecting lever 42 rotates in the A direction around the rotating shaft 42a and the elevator 46 is displaced to the reclining position. Meanwhile, as illustrated in FIG. 6B, the operating wire 44 is subjected to a pull operation when the operating lever 20 is operated to rotate the rotating drum 29A in the opposite direction, the elevator erecting lever 42 rotates around the rotating shaft 42a in the B direction which is opposite to the A direction, and the elevator 46 is displaced to the erecting position. Thus, by rotating the rotating shaft 42a through the elevator erecting lever 42 by the operation of the operating lever 20, the operating wire 44 can move (erect and recline) the elevator 46.

Figure 7:
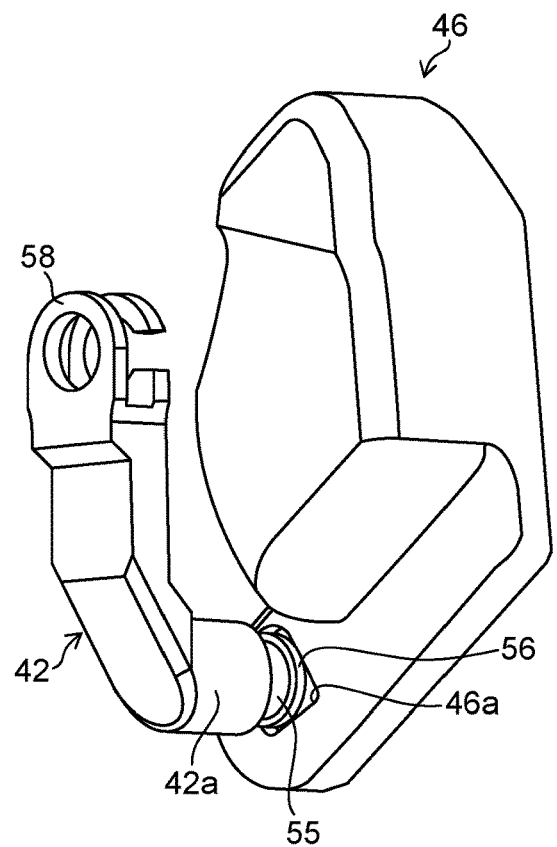
FIG. 7 is an external perspective view of an elevator erecting lever and the elevator.

FIG. 7 is an external perspective view of the elevator erecting lever 42 and the elevator 46. As illustrated in FIG. 7, in the elevator 46, a surface facing an opening portion of the treatment tool insertion channel 19 in the elevator housing chamber 38 is an arc-shaped guide surface (not illustrated) which guides a treatment tool, which is led from the treatment tool insertion channel 19 into the elevator housing chamber 38 toward the treatment tool exit port 38a. Moreover, a coupling hole 46a with which the rotating shaft 42a is coupled is formed on the proximal end portion of the elevator 46.

On the distal end side of the elevator erecting lever 42, a wire connection portion 58 which is coupled with the distal-end-side coupling portion 44a of the operating wire 44 guided into the erecting lever housing chamber 40 is formed, and the rotating shaft 42a is coupled (connected) with the proximal end side of the elevator erecting lever 42.

The rotating shaft 42a is inserted in the holding hole 50 from the side of the erecting lever housing chamber 40 and coupled with the coupling hole 46a of the elevator 46 in the elevator housing chamber 38 in a relativity unrotatable manner. By this means, the elevator 46 is coupled with one end of the rotating shaft 42a and the elevator erecting lever 42 is coupled with the other end of the rotating shaft 42a. The elevator 46 and the elevator erecting lever 42 are coupled in a relatively unrotatable manner through this rotating shaft 42a. Here, in the present embodiment, the other end side of the rotating shaft 42a has a polygonal shaft (rectangular shaft) shape and the coupling hole 46a has a shape to which the polygonal shaft fits. However, the shapes of the rotating shaft 42a and the coupling hole 46a are not especially limited. Moreover, the rotating shaft 42a includes an annular housing groove 55 which houses a ring-shaped seal member 54 (see FIG. 9), in an outer wall surface opposed to the inner wall surface of the holding hole 50.

Figure 8:
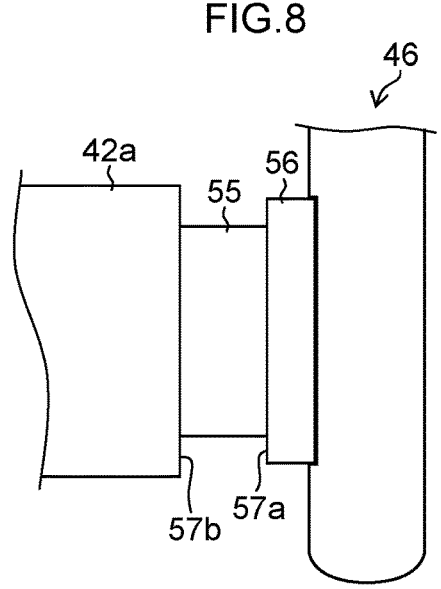
FIG. 8 is a side view of a region in which a housing groove of a rotating shaft is formed.

FIG. 8 is a side view of a region in which the housing groove 55 of the rotating shaft 42a is formed. As illustrated in FIG. 8, the housing groove 55 corresponds to the first engagement portion of the present invention and is engaged with the seal member 54 (see FIG. 9). Moreover, an opening edge portion of the housing groove 55 on the side of the elevator 46 (elevator side) includes a projection 56 which projects in a ring shape along the peripheral direction of the rotating shaft 42a.

The projection 56 includes a side wall surface 57a provided in a position opposed to a surface of the seal member 54 which is engaged with the housing groove 55, the surface of the seal member 54 facing the elevator 46. The side wall surface 57a functions as a restriction surface of the present invention that restricts the position of the seal member 54 in the axis direction of the rotating shaft 42a. Here, a side wall surface 57b of the housing groove 55 on the side of the elevator erecting lever 42 is provided in a position opposed to the surface of the seal member 54 facing the elevator erecting lever 42, and the side wall surface 57b functions as a restriction surface that restricts the position of the seal member 54 in the axis direction of the rotating shaft 42a in the same way as the side wall surface 57a. That is, in the present embodiment, the projection 56 and the housing groove 55 function as a seal member position restricting portion of the present invention.

Figure 9:
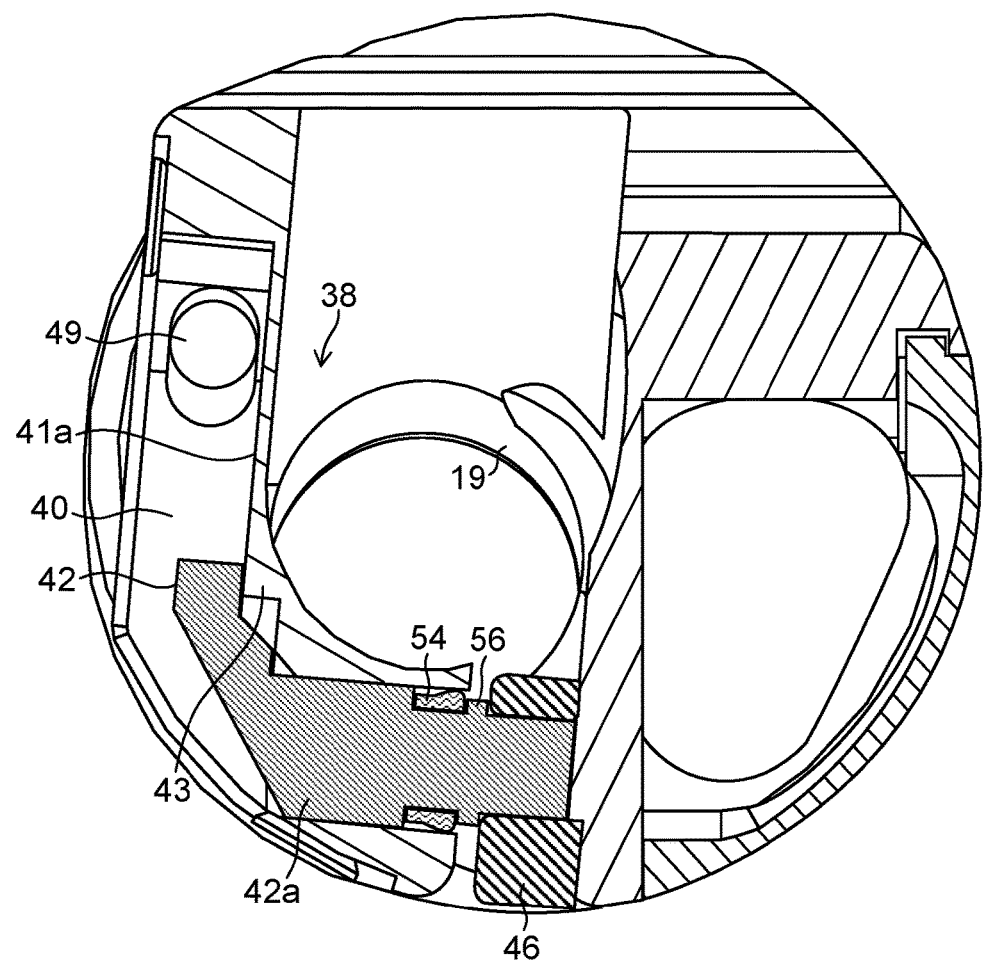
FIG. 9 is a cross-sectional view of the rotating shaft inserted in a holding hole.
Figure 10:
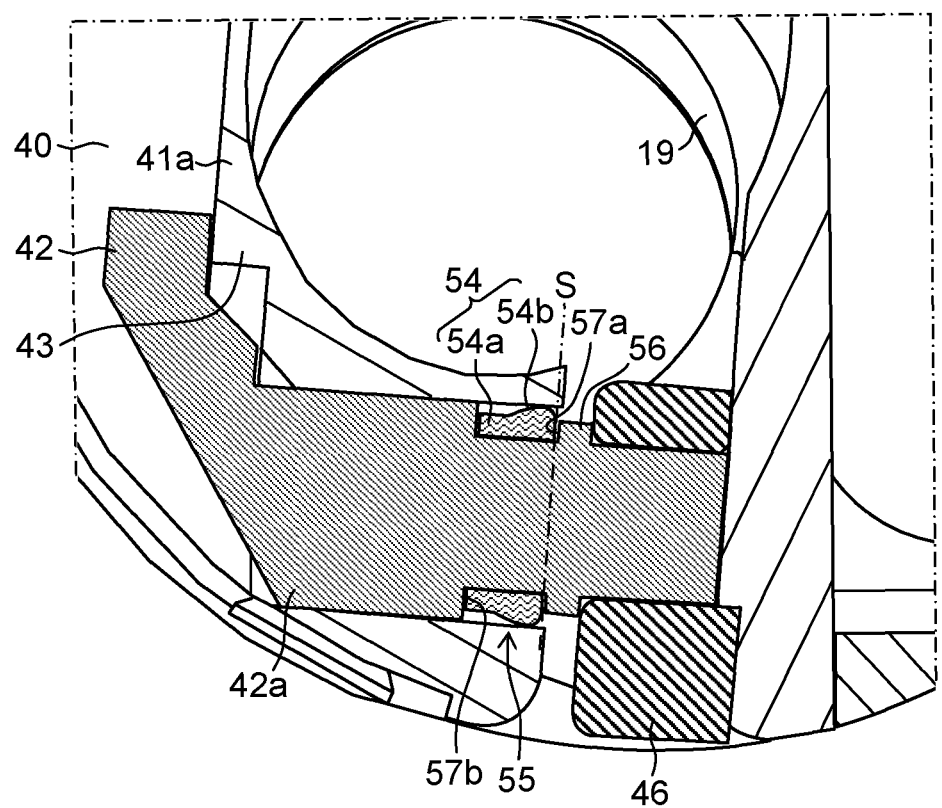
FIG. 10 is an enlarged which enlarges a part of the cross-sectional view illustrated in FIG. 9.

FIG. 9 is a cross-sectional view of the rotating shaft 42a inserted in the holding hole 50. FIG. 10 is an enlarged view that expands a portion of the cross-sectional view illustrated in FIG. 9. As illustrated in FIGS. 9 and 10, the ring-shaped seal member 54 housed in the housing groove 55 is disposed between the holding hole 50 and the rotating shaft 42a, and the seal member 54 is engaged with the housing groove 55. That is, part of the outer peripheral surface of the seal member 54 functions as a second engagement portion of the present invention which is engaged with the housing groove 55.

The seal member 54 includes a first thick portion 54a and a second thick portion 54b disposed on the side of the elevator 46 with respect to (from) the first thick portion 54a. The second thick portion 54b is configured in which the thickness in a direction perpendicular to the axis direction of the rotating shaft 42a is thicker than the first thick portion 54a. In the present embodiment, the position of the rotating shaft 42a (housing groove 55) in the axis direction with respect to the holding hole 50 is restricted by the first partition wall 41a such that a part of the second thick portion 54b is exposed from an opening portion on the side of the elevator 46 of the holding hole 50 (hereinafter simply referred to as "opening portion of the holding hole 50") to a surface side facing the elevator 46, of the first partition wall 41a.

The first partition wall 41a includes a corner portion 43 formed by the bottom surface of the concave erecting lever housing chamber 40 and the inner wall surface of the holding hole 50. The corner portion 43 corresponds to a rotating shaft position restricting portion of the present invention. When the housing groove 55 of the rotating shaft 42a inserted in the holding hole 50 from the side of the erecting lever housing chamber 40 reaches the vicinity of the opening portion of the holding hole 50, this corner portion 43 abuts on the elevator erecting lever 42 which is integrated with the rotating shaft 42a so as to restrict further insertion of the rotating shaft 42a. By this means, the position of the rotating shaft 42*a* (housing groove 55) in the axis direction with respect to the holding hole 50 is restricted by the corner portion 43, and the housing groove 55 is positioned (located) in the vicinity of the opening portion of the holding hole 50.

An airtight surface S is formed in the position of the opening portion of the holding hole 50 by the seal member 54 which is engaged with the housing groove 55. Further, by this airtight surface S, a liquid such as a blood or water entering in the elevator housing chamber 38 (hereinafter simply abbreviated as "liquid") is prevented from entering between the inner wall surface of the holding hole 50 and the outer wall surface of the rotating shaft 42*a*.

Moreover, by the side wall surface 57*a* of the projection 56 and the side wall surface 57*b* of the housing groove 55, the position of the seal member 54 in the axis direction of the rotating shaft 42*a* is restricted to a position in which a part of the second thick portion 54*b* is exposed to the surface side facing the elevator 46 of the first partition wall 41*a*. By this means, the seal member 54 is prevented from moving in the axis direction of the rotating shaft 42*a* by the rotation of the rotating shaft 42*a* or by the slide contact with the inner wall surface of the holding hole 50, and a state in which a part of the second thick portion 54*b* is exposed to the surface side facing the elevator 46 of the first partition wall 41*a* is maintained. As a result, a liquid entering in the elevator housing chamber 38 is reliably prevented from entering between the inner wall surface of the holding hole 50 and the outer wall surface of the rotating shaft 42*a*.

Figure 11:
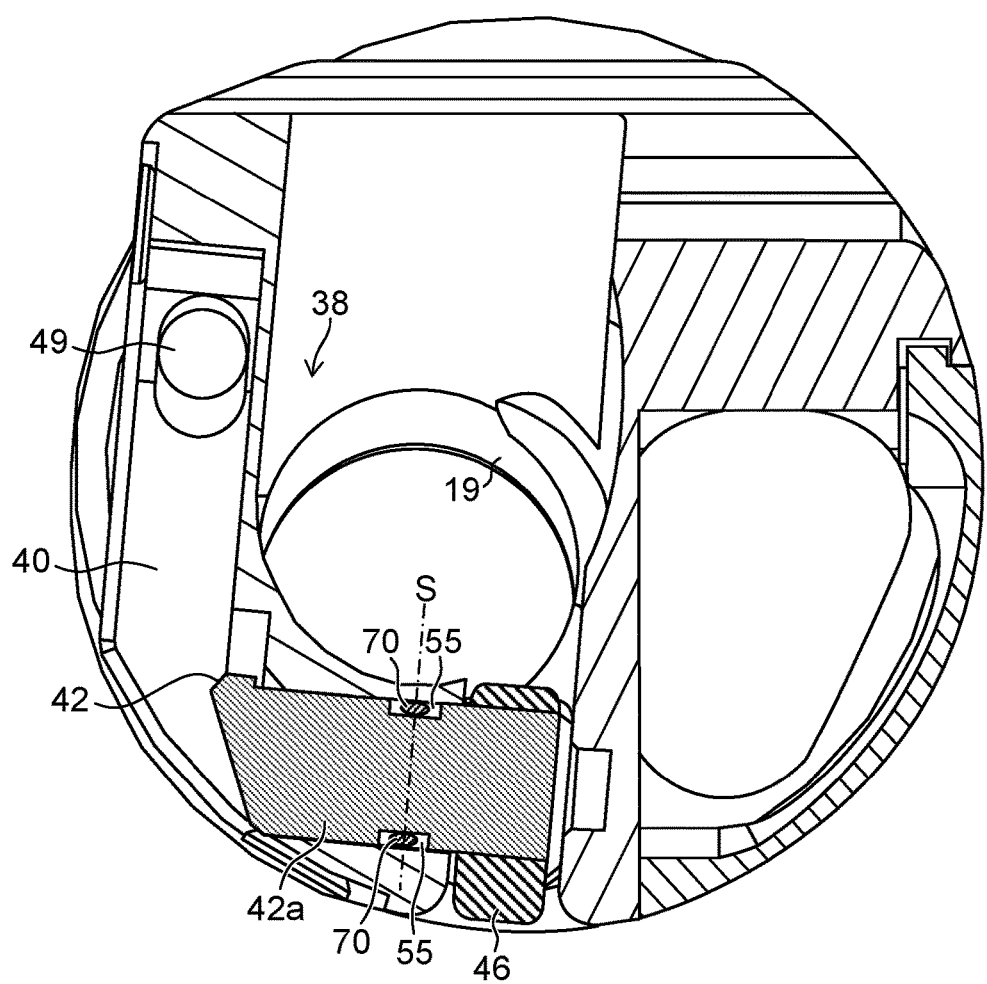
FIG. 11 is a cross-sectional view of a rotating shaft of a comparative example.

Meanwhile, in FIG. 11 illustrating a comparative example, the position of a seal member 70 shifts toward the side of the elevator erecting lever 42 as compared with the present embodiment, and, if a part of the seal member 70 is not exposed to the side of the surface facing the elevator 46 of the first partition wall 41*a*, the position of the airtight surface S shifts from the position of the opening portion of the holding hole 50 toward the side of the elevator erecting lever 42. As a result, since there is a possibility that a liquid entering in the elevator housing chamber 38 enters between the inner wall surface of the holding hole 50 and the outer wall surface of the rotating shaft 42*a*, it is necessary to take time and labor for the cleaning processing of the fitting portion between the holding hole 50 and the rotating shaft 42*a*.

As compared with such a comparative example, in the present embodiment, a liquid is prevented from entering between the inner wall surface of the holding hole 50 and the outer wall surface of the rotating shaft 42*a* by the seal member 54, a part of which is exposed to the surface side facing the elevator 46 of the first partition wall 41*a*. As a result, since dirt becomes less likely to be accumulated in the fitting portion between the holding hole 50 and the rotating shaft 42*a*, it is not necessary to take time and labor for the cleaning processing of the fitting portion between the holding hole 50 and the rotating shaft 42*a* compared to conventional art. Therefore, it is possible to reduce the time and labor taken for the cleaning processing.

Modification Example 1 and Modification Example 2

Figure 12:
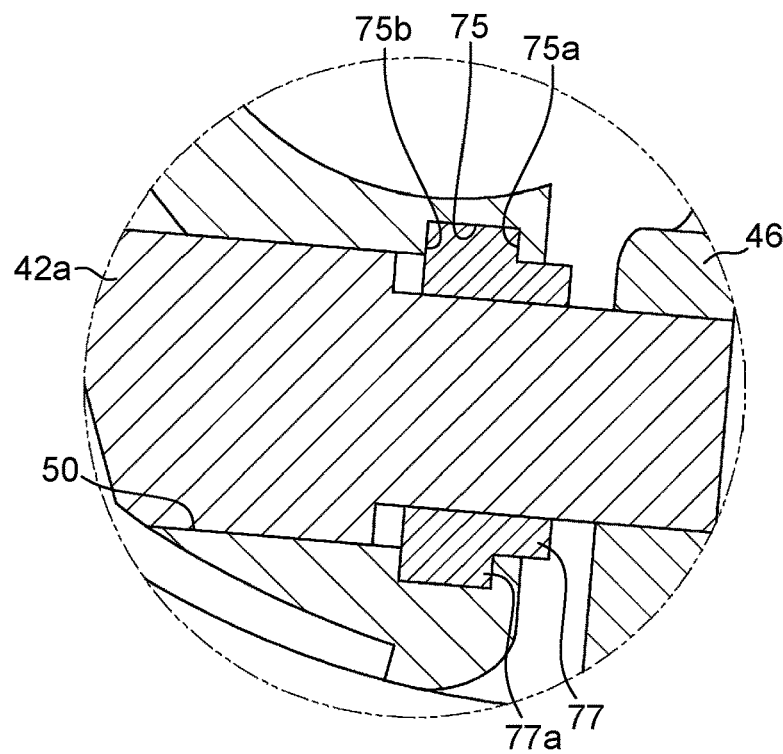
FIG. 12 is a cross-sectional view of a holding hole according to a modification example 1 in which a concave engagement portion is formed.

The seal member 54 is engaged with the housing groove 55 of the rotating shaft 42*a* in the above-mentioned embodiment, but an engagement portion engaged with the seal member 54 may be provided in the inner wall surface of the holding hole 50 of the first partition wall 41*a*. FIG. 12 is a cross-sectional view of the holding hole 50 according to a modification example 1 in which a concave engagement portion 75 that is a concave-shaped engagement portion is formed. Moreover, FIG. 13 is a cross-sectional view of the holding hole 50 according to a modification example 2 in which a convex engagement portion 80 that is a convex-shaped engagement portion is formed.

As illustrated in FIG. 12, in the modification example 1, a convex-shaped convex engagement portion 77*a* (corresponding to the second engagement portion of the present invention) formed along the outer peripheral surface of a ring-shaped seal member 77 is engaged with a concave portion of the ring-shaped concave engagement portion 75 (corresponding to the first engagement portion and seal member position restricting portion of the present invention) formed along the peripheral direction of the inner wall surface of the holding hole 50 of the first partition wall 41*a*. At this time, the formation position of the concave engagement portion 75 is adjusted such that a part of the seal member 77 is exposed from the opening portion of the holding hole 50 to the surface side facing the elevator 46 of the first partition wall 41*a*.

The concave engagement portion 75 includes a side wall surface 75*a* opposed to a surface facing the side of the elevator 46 of the convex engagement portion 77*a*, and a side wall surface 75*b* opposed to a surface facing the side of the elevator erecting lever 42 of the convex engagement portion 77*a*. Therefore, when the side wall surfaces 75*a* and 75*b* of the concave engagement portion 75 function as a restriction surface which restricts the position of the seal member 77 in the axis direction of the rotating shaft 42*a*, a state in which the part of the seal member 77 is exposed to the surface side facing the elevator 46 of the first partition wall 41*a* is maintained.

Figure 13:
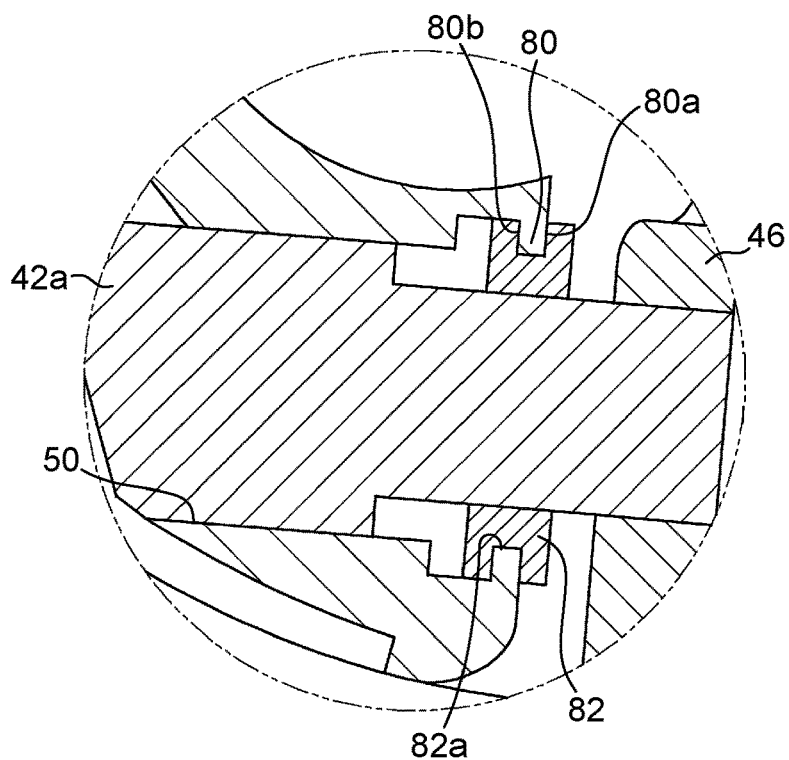
FIG. 13 is a cross-sectional view of a holding hole according to a modification example 2 in which a convex engagement portion is formed.

As illustrated in FIG. 13, in the modification example 2, a convex engagement portion 80 (corresponding to the first engagement portion and seal member position restricting portion of the present invention) formed along the peripheral direction in the inner wall surface of the holding hole 50 of the first partition wall 41*a* is engaged with a concave-shaped concave engagement portion 82*a* (corresponding to the second engagement portion of the present invention) formed along the peripheral direction in the outer peripheral surface of a ring-shaped seal member 82. At this time, the formation position of the convex engagement portion 80 is adjusted such that a part of the seal member 82 is exposed from the opening on the side of the elevator 46 of the holding hole 50 to the surface side facing the elevator 46 of the first partition wall 41*a*.

The convex engagement portion 80 includes a side wall surface 80*a* opposed to a surface (side wall surface) facing the side of the elevator 46 of the concave engagement portion 82*a*, and a side wall surface 80*b* opposed to a surface (side wall surface) facing the side of the elevator erecting lever 42 of the concave engagement portion 82*a*. Therefore, when the side wall surfaces 80*a* and 80*b* of the convex engagement portion 80 function as a restriction surface which restricts the position of the seal member 82 in the axis direction of the rotating shaft 42*a*, a state in which the part of the seal member 82 is exposed to the surface side facing the elevator 46 of the first partition wall 41*a* is maintained.

Modification Example 3

In the above-mentioned embodiment, since the coupling position between the rotating shaft 42*a* and the elevator 46 is located on the side of the elevator housing chamber 38 from (with respect to) the airtight surface S, there is a possibility that a liquid entering in the elevator housing chamber 38 contacts with the fitting portion between the coupling hole 46a of the elevator 46 and the rotating shaft 42a, and it becomes necessary to take time and labor for cleaning processing of the fitting portion between the coupling hole 46a and the rotating shaft 42a.

Figure 14:
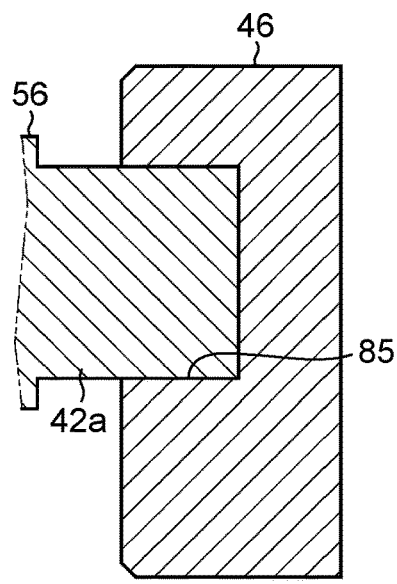
FIG. 14 is a cross-sectional view of an elevator according to a modification example 3 in which it is possible to reduce the time and labor of cleaning processing.

FIG. 14 is a cross-sectional view of the elevator 46 according to a modification example 3 in which it is possible to reduce labor and time for cleaning processing. As illustrated in FIG. 14, a coupling hole 85 is formed in the elevator 46 so as to extend from a facing surface facing the holding hole 50 of the elevator 46 to the inside of the elevator 46, and this facing surface does not penetrate to an opposite surface on the side opposite to the facing surface. Therefore, the distal end portion of the rotating shaft 42a coupled with the coupling hole 85 is not exposed from the opposite surface of the elevator 46. As a result, a liquid is prevented from entering from the opposite surface side of the elevator 46 to a space between the inner wall surface of the coupling hole 85 and the outer wall surface of the rotating shaft 42a.

Moreover, as for the gap between the inner wall surface of the coupling hole 85 and the outer wall surface of the rotating shaft 42a, since one end of the gap in the axis direction of the rotating shaft 42a is closed, a liquid becomes less likely to enter in the gap as compared with a state in which both ends of the gap are opened. By this means, dirt becomes less likely to be accumulated in the fitting portion between the coupling hole 85 and the rotating shaft 42a, and it is possible to reduce time and labor taken for cleaning processing.

Modification Example 4

Figure 15:
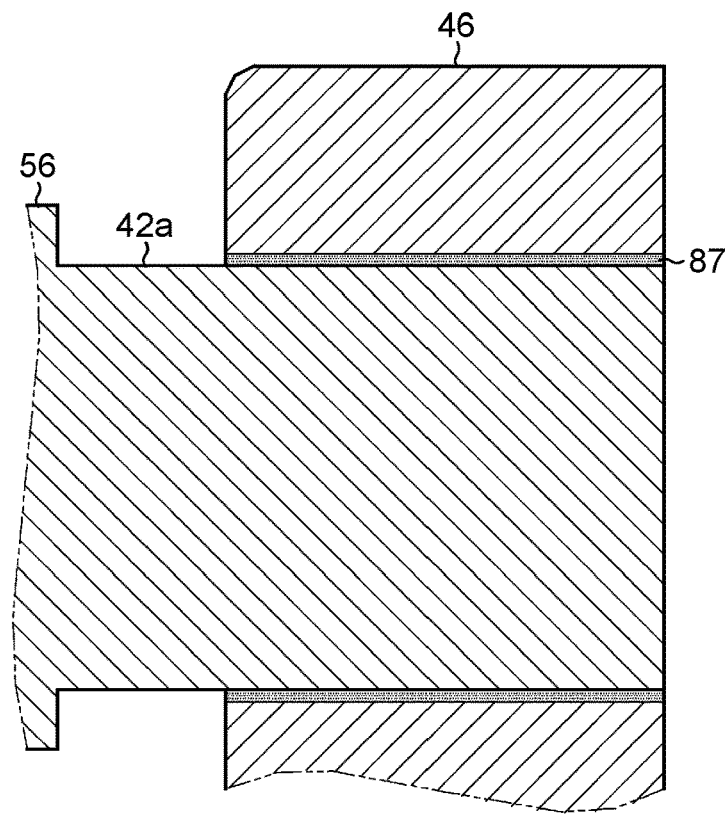
FIG. 15 is a cross-sectional view of an elevator according to a modification example 4 in which it is possible to reduce the time and labor of cleaning processing.

In the above-mentioned modification example 3, the coupling hole 85 of a non-through-hole shape is formed in the elevator 46 to reduce labor and time for cleaning processing of the fitting portion between the coupling hole 85 of the elevator 46 and the rotating shaft 42a, but, in a modification example 4, the coupling hole 46a of a through-hole shape is formed in the elevator 46 in the same way as the above-mentioned embodiment. FIG. 15 is a cross-sectional view of the elevator 46 according to the modification example 4 in which it is possible to reduce labor and time for cleaning processing.

As illustrated in FIG. 15, in the modification example 4, a seal agent 87 is applied or filled between the inner wall surface of the coupling hole 46a and the outer wall surface of the rotating shaft 42a. By this seal agent 87, a liquid is prevented from entering the gap between the inner wall surface of the coupling hole 46a and the outer wall surface of the rotating shaft 42a. By this means, dirt becomes less likely to be accumulated in the fitting portion between the coupling hole 46a and the rotating shaft 42a, and it is possible to reduce time and labor taken for cleaning processing.

<Others>

One example of various engagement portions (the first engagement portion of the present invention) provided on the outer wall surface of the rotating shaft 42a or the inner wall surface of the holding hole 50 and an engagement portion (the second engagement portion of the present invention) provided in a seal member have been described in each above-mentioned embodiment, but the shape and structure of these first engagement portion and second engagement portion are not specifically limited. Moreover, the first engagement portion functions as a seal member position restricting portion in each above-mentioned embodiment, but the seal member position restricting portion may be a discrete body which is separated from the first engagement portion.

Explanation has been given using a side-view endoscope as an example in each above-mentioned embodiment, but the present invention is applicable to various endoscopes such as an ultrasonic endoscope and a direct-view endoscope which include an elevator that adjusts the derivation direction of a treatment tool in the distal end portion of an insertion portion.

What is claimed is:
1. An endoscope comprising:
an insertion portion which includes a distal end and a proximal end;
an operation portion which is provided on a proximal end side of the insertion portion and includes an operating member;
a distal end portion body which is provided on a distal end side of the insertion portion;
a rotating shaft which is rotatably supported in the distal end portion body;
an elevator which is coupled with one end of the rotating shaft;
an elevator erecting lever which is coupled with the other end of the rotating shaft;
an operating wire which includes a proximal-end-side coupling portion coupled with the operating member and a distal-end-side coupling portion coupled with the elevator erecting lever, the operation wire configured to rotate the rotating shaft through the elevator erecting lever by operation of the operating member to erect the elevator;
a partition wall which includes a holding hole configured to support the rotating shaft, is a part of the distal end portion body and is provided between the elevator and the elevator erecting lever; and
a seal member which is disposed between the holding hole and the rotating shaft, at least part of the seal member being exposed to a surface side facing the elevator of the partition wall,
wherein:
the partition wall includes a first engagement portion formed along a peripheral direction in an inner wall surface of the holding hole;
the seal member includes a second engagement portion along an outer peripheral surface of the seal member, and the second engagement portion is configured to engage with the first engagement portion;
the first engagement portion and the second engagement portion have complementary shaped portions to be fitted with each other; and
a formation position of the first engagement portion is positioned such that the exposed part of the seal member is protruded from an opening portion of the holding hole to the surface side facing the elevator of the partition wall,
wherein the seal member comprises:
a first thick portion; and
a second thick portion which has a thickness thicker than the first thick portion in a direction perpendicular to an axis direction of the rotating shaft,
wherein the first engagement portion includes:
a first side wall surface, being opposed to a surface facing a side of the elevator of the second engagement portion; and a second side wall surface, being opposed to a surface facing a side of the elevator erecting lever of the second engagement portion,
wherein the first engagement portion and the second engagement portion are fitted with each other at the first side wall surface and the second side wall surface.

2. An endoscope comprising:
an insertion portion which includes a distal end and a proximal end;
an operation portion which is provided on a proximal end side of the insertion portion and includes an operating member;
a distal end portion body which is provided on a distal end side of the insertion portion;
a rotating shaft which is rotatably supported in the distal end portion body;
an elevator which is coupled with one end of the rotating shaft;
an elevator erecting lever which is coupled with the other end of the rotating shaft;
an operating wire which includes a proximal-end-side coupling portion coupled with the operating member and a distal-end-side coupling portion coupled with the elevator erecting lever, the operation wire configured to rotate the rotating shaft through the elevator erecting lever by operation of the operating member to erect the elevator;
a partition wall which includes a holding hole configured to support the rotating shaft, is a part of the distal end portion body and is provided between the elevator and the elevator erecting lever; and
a seal member which is disposed between the holding hole and the rotating shaft, at least part of the seal member being exposed to a surface side facing the elevator of the partition wall,
wherein:
the rotating shaft includes a housing groove for housing the seal member and an enlarged diameter portion disposed between the housing groove and the elevator;
the housing groove and the enlarged diameter portion are disposed on an outer wall surface of the rotating shaft facing an inner wall surface of the holding hole;
the seal member includes a second engagement portion configured to engage with the enlarged diameter portion;
the partition wall includes a rotating shaft position restricting portion configured to restrict a position of the rotating shaft in an axis direction with respect to the holding hole; and
a position of the rotating shaft in the axis direction with respect to the holding hole is restricted by the partition wall such that a part of the enlarged diameter portion is exposed from an opening portion on a side of the elevator of the holding hole to the surface side facing the elevator, of the partition wall,
wherein the seal member comprises:
a first thick portion; and
a second thick portion which has a thickness thicker than the first thick portion in a direction perpendicular to an axis direction of the rotating shaft,
wherein the enlarged diameter portion projects in a ring shape along a peripheral direction of the rotating shaft, and the enlarged diameter portion includes a first side wall surface provided in a position opposed to a surface of the seal member,
a second side wall surface of the housing groove on a side of the elevator erecting lever is provided in a position opposed to a surface of the seal member facing the elevator erecting lever,
by the first side wall surface and the second side wall surface, a position of the seal member in the axis direction of the rotating shaft is restricted to a position in which a part of the second thick portion is exposed to a surface side facing the elevator of the partition wall.

3. The endoscope according to claim 1, wherein the first engagement portion includes a seal member position restricting portion configured to restrict a movement of the seal member in a direction approaching the elevator and in an axis direction of the rotating shaft.

4. The endoscope according to claim 3, wherein the seal member position restricting portion includes a restriction surface which is provided in a position opposed to a surface of the seal member facing the elevator, and the restriction surface restricts the position of the seal member in the axis direction of the rotating shaft.

5. The endoscope according to claim 1, wherein:
the second thick portion is disposed on a side of the elevator with respect to the first thick portion.

6. The endoscope according to claim 2, wherein:
the second thick portion is disposed on a side of the elevator with respect to the first thick portion.

7. The endoscope according to claim 2, wherein the enlarged diameter portion includes a seal member position restricting portion configured to restrict a movement of the seal member in a direction approaching the elevator and in an axis direction of the rotating shaft.

8. The endoscope according to claim 1, wherein:
the first engagement portion includes a concave-shaped portion; and
the seal member includes a convex-shaped portion as the second engagement portion that is engaged with the concave-shaped portion of the first engagement portion.

9. The endoscope according to claim 1, wherein:
the first engagement portion includes a convex-shaped portion; and
the seal member includes a concave-shaped portion as the second engagement portion that is engaged with the convex-shaped portion of the first engagement portion.

10. The endoscope according to claim 2, wherein the enlarged diameter portion is positioned outside of the holding hole that is formed on the partition wall and configured to support the rotating shaft.

* * * * *